United States Patent [19]
Hanson et al.

[11] Patent Number: 5,286,635
[45] Date of Patent: Feb. 15, 1994

[54] GENETICALLY TRANSFORMED PEA PLANTS AND METHODS FOR THEIR PRODUCTION

[75] Inventors: William Hanson, San Francisco; Alison Morgan, Fremont; Karol E. P. Robinson, Moraga; Karen L. Ruby, Berkeley, all of Calif.

[73] Assignee: FreshWorld, L.P., Doylestown, Pa.

[21] Appl. No.: 764,583

[22] Filed: Sep. 24, 1991

[51] Int. Cl.$^5$ .................. C12N 15/00; C12N 5/00; A01H 1/04
[52] U.S. Cl. .................. 435/172.3; 435/240.45; 800/205; 800/DIG. 23
[58] Field of Search .................. 800/205; 435/172.3, 435/240.45, 240.48, 240.49, 240.5, 240.51

[56] References Cited

PUBLICATIONS

Naverby, B., et al. Plant Cell Reports, vol. 9, (Apr. 1991) pp. 676–679.
Jackson, J. A., et al. In vitro Cell. Dev. Biol., vol. 26 (Aug. 1990) pp. 835–838.
Puonti-Kaerlas, J., et al. Theor. Appl. Genet., vol. 80 (Aug. 1990) pp. 246–252.
Bolton, G. W., et al. Science, vol. 232 (1986) pp. 983–985.
Lee, K. Y., et al. The EMBO Journal, vol. 7 (1988) pp. 1241–1248.
De Kathen, A. et al. Plant Cell Reports, vol. 9 (1990) pp. 276–279.
Puonti-Kaerlas, J., et al Plant Cell Reports, vol. 8 (1989) pp. 321–324.
DeKathen et al. (1990) *J. Cell Biochem.*, Suppl. O (14 Part E), Abstract R125, p. 282.
PBI Bulletin, May 1991 NRC Plant Biotech. Institute, National Research Council Canada, pp. 2–4.
Jordan et al., (1990) *J. Cell Biochem.*, Suppl. O (14 Part E) Abstract R126, p. 282.
Lulsdorf et al. (1991) *Plant Cell Rep.*, 9:479–483.
Hussey et al. (1989) 148:101–105.
Filipone et al. (1988) *Genet. Agrar.*, 42:452, Abstract.
Hinchee et al. (1988) *Bio/Technology*, 6:915–922 (soybean).
Eapen et al. (1987) *Theor. Appl. Genet.*, 75:207–210.

*Primary Examiner*—David T. Fox
*Assistant Examiner*—Charles Rories
*Attorney, Agent, or Firm*—Townsend and Townsend Khourie and Crew

[57] ABSTRACT

Pea explant material is transformed by incubation with Agrobacterium cells carrying an exogenous DNA sequence. The pea explant is preferably obtained from the plumule of a pea seed, and transformed shoots are preferably induced directly in the explant material without passage through a callus phase. Whole transformed pea plants may be regenerated from the transformed shoots by rooting and subsequent planting in the soil. The exogenous DNA will be stably incorporated into the chromosomes of the regenerated pea plant which will be able to express gene(s) encoded by the DNA sequence.

23 Claims, 4 Drawing Sheets

FIG. 1.

CROSS-HATCHING INDICATES A PREFERRED PART OF PLUMULE

GENETICALLY TRANSFORMED PEA PLANTS AND METHODS FOR THEIR PRODUCTION

BACKGROUND OF THE INVENTION

1. Field of the Invention

The present invention relates generally to methods for genetically altering higher plant materials and reproducing whole plants therefrom. More particularly, the invention relates to a method for genetically transforming pea plants.

The garden pea (*Pisum sativum* L.) is a legume and an important food crop. As with other legumes, pea plants are able to obtain nitrogen from symbiotic soil bacteria and have a substantially reduced fertilizer requirement compared to other non-leguminous crops. Thus, the production of new, improved cultivars of pea could be of great commercial value, particularly in view of increasing fertilizer costs.

As with any valuable plant species, breeders have long used conventional cross-breeding techniques to improve existing varieties and create new cultivars. While improvements have been achieved, cross-breeding techniques are laborious and slow because of the time required to breed and grow successive plant generations.

Conventional breeding methods can only utilize those genes that are present in species that are sexually compatible with P. sativum. Thus, it would be desirable to utilize recombinant DNA technology to produce new pea varieties and cultivars in a controlled and predictable manner that contain genes both from sexually compatible crops, and from other unrelated plants, animals, bacteria and viruses.

The recombinant DNA manipulation of pea, however, has been hindered by difficulty in regenerating whole plants from tissue culture, by difficulty in obtaining transformed pea tissue and ultimately, in linking regeneration with transformation.

For these reasons, it would be desirable to provide improved methods for the recombinant DNA transformation of pea plant material and the regeneration of whole plants from the transformed material. It would be particularly desirable to be able to introduce desired characteristic(s) to such material(s) and to be able to regenerate viable pea plantlets from the modified materials. Such methods should be capable of introducing a preselected exogenous gene(s) into the pea plant material and should permit the selection of transformed shoots which are regenerated from the material. The method should produce regenerated pea plants which have stably incorporated the gene(s).

2. Description of the Background Art

DeKathen et al. (1990) Plant Cell Rep. 9:276–279, describes the Agrobacterium-mediated transformation of epicotyl and nodus explants from Madria (an inedible pod variety of pea). Related work was described in DeKathen et al. (1990) J. Cell Biochem., Suppl. O (14 Part E), Abstract R125, p. 282. Puonti-Kaerlas et al. (1990) Theor. and Appl. Genet. 80:246–252, describes the regeneration of transformed shoots from transformed callus material of two inedible pod varieties of pea.

Jackson and Hobbs (1990) In Vitro Cell. Dev. Biol. 26:835–838, describes the regeneration of whole plants from pea plumule material, without transformation. PBI Bulletin, May 1991, NRC Plant Biotechnology Institute, National Research Council Canada, pp 2–4, asserts that the culture method of Jackson and Hobbs has been used for the transformation of pea with Agrobacterium vectors. See, Jordan et al. (1990) J. Cell Biochem., Suppl. O (14 Part E), Abstract R126, p. 282.

Transformation of pea plant material without whole plant regeneration is described in Lulsdorf et al. (1991) Plant Cell Rep. 9:479–483; Puonti-Kaerlas (1989) Plant Cell Rep. 8:321–324; Hussey et al. (1989) 148:101–105; Filipone and Lurquin (1988) Genet. Agrar. 42:452 (Abstract); and Nauerby et al. (1991) Plant Cell Rep. 9:676–679.

The transformation of legumes other than pea is described in Hinchee et al. (1988) Bio/Technology 6:915–922 (soybean); and Eapen et al. (1987) Theor. Appl. Genet. 75:207–210.

SUMMARY OF THE INVENTION

The present invention comprises methods for the genetic transformation of pea plant material and for producing and selecting viable shoots from the material which express an exogenous DNA sequence which has been introduced. Whole pea plants expressing the exogenous DNA sequence may be produced by rooting the shoot and subsequently planting the rooted shoot in soil. The pea plant material is transformed by incubation with Agrobacterium cells carrying the exogenous DNA sequence which typically includes a selectable plant marker gene as well as one or more genes to be expressed. Shoots are regenerated from the pea plant material and selected, typically by growth on a selection and regeneration medium which inhibits growth in the absence of the marker.

In a first aspect of the present invention, the pea plant material is derived from the plumule, which is an embryonic shoot from a pea seed, preferably being the lower portion of plumule including the cotyledonary nodes which are closest to the seed. Use of the plumule as the plant material to be transformed is advantageous because the plumule is highly regenerable and produces large numbers of shoots when placed on a regeneration medium. The highly regenerable nature of the plumule increases the probability of transformed cells regenerating to give transformed plants.

In a second aspect of the present invention, the transformed regenerated shoot is obtained from non-callus plant material. That is, the pea plant material is transformed and regenerated under conditions which produce transformed shoots which do not pass through a callus stage of development. The avoidance of the callus stage is advantageous because it decreases the time needed to obtain a transformed plant. Moreover, it increases the efficiency of transformation, and it reduces the risk of somaclonal variation due to mutations accumulating in the callus due to extended culture times.

other preferred aspects of the present invention include the use of a plant selectable marker selected from the group consisting of the aadA gene which encodes spectinomycin resistance, the SPT gene which encodes streptomycin resistance, and the ALS gene which encodes chlorsulfuron resistance, as well as the use of 6-benzyladenine (6-BA) to induce shoot formation in the regeneration medium.

The present invention further comprises transformed shoots and whole plant materials produced by the above pea transformation methods.

The methods of the present invention provide a particularly convenient technique for selectably breeding new pea cultivars in a predictable and expeditious manner. It is expected that a variety of traits, such as morphology, herbicide resistance, pesticide resistance, disease resistance, environmental tolerance (e.g., temperature, drought, salinity), growth characteristics, nutritional content, taste, and the like, may be intentionally introduced into the regenerated shoots and stably incorporated into the chromosomes of the regenerated whole plants. The methods of the present invention will be suitable for all or most types of garden peas, including both edible pod and inedible pod varieties, being particularly suitable for edible pod varieties.

BRIEF DESCRIPTION OF THE DRAWINGS

FIG. 3 is a plasmid map of pJJ4383. The restriction sites in FIGS. 3-6 are designated: B-BamHI Bg-BglII; C-ClaI; E-EcoRI; H-HindIII; Hp-HpaI; K-KpnI; N-NotI; Nc-NcoI; P-PstI; Sl-SstI; Sa-SalI; Sm-smaI; Xb-XbaI; and Xh-XhoI.

DESCRIPTION OF THE SPECIFIC EMBODIMENTS

According to the present invention, genetically transformed pea plants are obtained by the selective introduction of exogenous DNA sequence(s) into the chromosomes of cultured pea plant material. The methods require certain starting materials, including pea explant material, the DNA sequence(s) to be introduced, Agrobacterium cells to carry the DNA sequence(s) and mediate their transfer to the pea explant material, and culture media suitable for the steps of cocultivation of pea explant material and Agrobacterium cells, shoot regeneration from transformed explant material, shoot selection, and rooting of selected shoots. Each of the necessary starting materials will be described below in connection with the method of the present invention.

Figure 1:
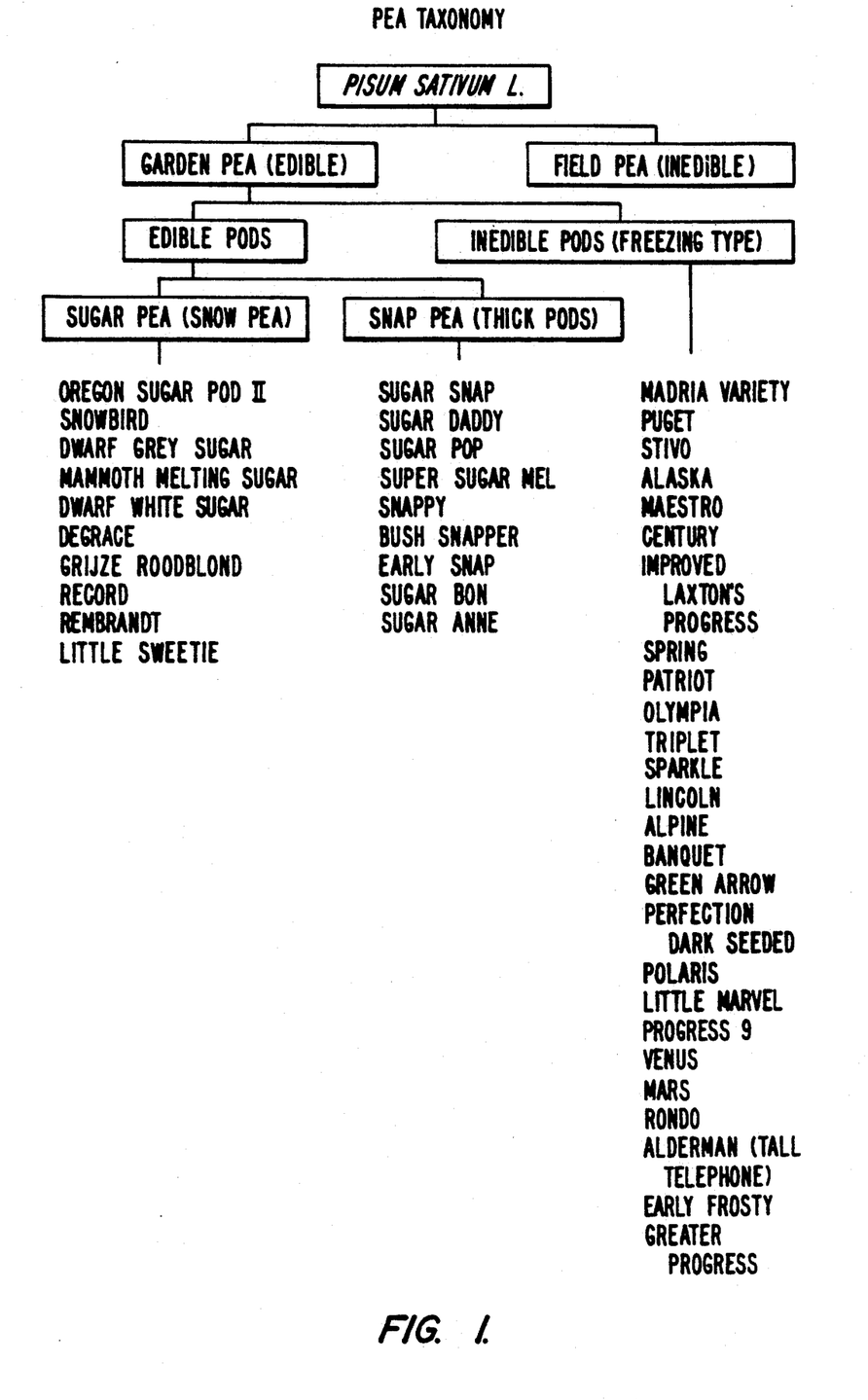
FIG. 1 illustrates the taxonomy of pea (*Pisum sativum* L.).

Pea explant material suitable for use in the present invention may be obtained from virtually any variety or cultivar of the pea species, *Pisum sativum* L., with illustrative varieties listed in the taxonomical chart of FIG. 1. The transformation method is suitable for both the field pea (inedible) and the garden pea (edible), with the transformation of edible garden peas being preferred. The edible garden peas include both edible pod cultivars and inedible pod cultivars, with particular cultivars falling into each class being listed in FIG. 1.

The explant material to be transformed may be obtained from any plant part that is capable of regenerating shoots, including leaf, stem, petiole, shoot tips, peduncle, and cotyledon, with portions of the seed being preferred. The seed may be mature or immature, preferably being mature. "Mature" means that the seeds have developed on the plant to full size, have dried, and are capable of germinating independently. "Immature" means that the seeds have developed on the plant to less than full size, remain green, and are not capable of germinating without exposure to inducing compounds.

The explant material is preferably embryonic tissue obtained from sterilized seed. Embryonic tissues are prepared by removing the seed coat from sterilized seed, cutting off the cotyledons where they are attached to the embryo and cutting each tissue into approximately 0.5 cm segments.

Leaf, petiole, and stem explants may be obtained from seedlings after germination of sterilized seed on germination medium. This is the same as general pea medium (as described below), with MS salts at ½ concentration, B5 vitamins, and sucrose as an energy source (preferably at 5 g/l). No auxins or cytokinins are added. A preferred germination medium is PGM, as described in detail in the Experimental section hereinafter. Sterilized seed are placed on germination tit medium and cultured at 20-250° C., in a light regime where during each day of the culture period, the seeds are cultured for 16 hrs at 1500-3000 lux under plant spectrum lights and for 8 hrs in a dark growth room. When the seedling is approximately 5 cm tall, the leaf, petioles and stems are cut into approximately 0.5 cm segments.

Figure 2:
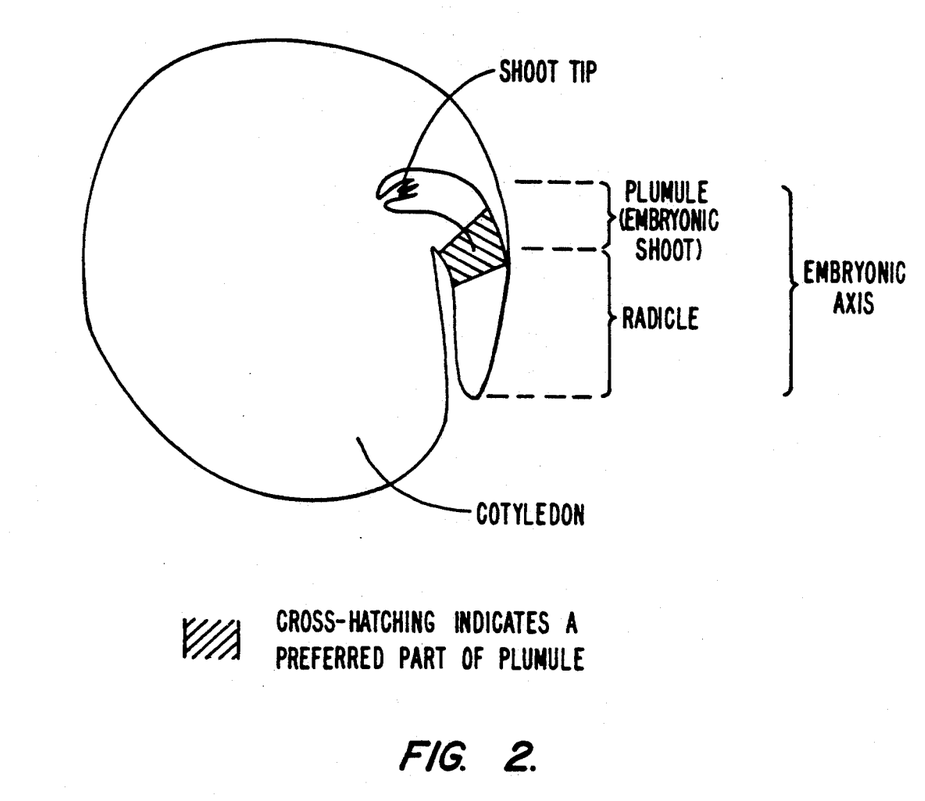
FIG. 2 is a side view of pea seed with the coat and top cotyledon removed where the preferred source of explant material is identified.

The preferred pea explant material for use in the present invention is the embryonic shoot, referred to as a plumule, which extends from and includes the cotyledonary nodes of the seed, as illustrated in FIG. 2. Use of the lower portion of the plumule between the shoot tip and including the cotyledonary nodes is particularly preferred because the lower part of the plumule is the most regenerable part of the plumule. The extreme tip of the plumule is less regenerable and it also encompasses the shoot meristem. Inclusion of the shoot meristem would lead to nontransformed shoots developing as the meristem grew.

The exogenous DNA sequences to be introduced may be obtained from virtually any source, including bacterial, algal, fungal, foreign plant, endogenous pea plant, and animal, and will usually include at least one selectable plant marker gene to permit screening and selection of transformed callus cells (i.e., those cells which have incorporated the exogenous DNA into their chromosomes), as well as one or more "functional" genes which are chosen to provide, enhance, suppress, or otherwise modify expression of a desired trait or phenotype in the resulting plant. Such traits include herbicide resistance, pesticide resistance, disease resistance, environmental tolerance (e.g., temperature, drought, salinity), morphology, growth characteristics, nutritional content, taste, yield, horticultural characteristics, consumer values, and the like.

The functional gene to be introduced may be a structural gene which encodes a polypeptide which imparts the desired phenotype. Alternatively, the functional gene may be a regulatory gene which might play a role in transcriptional and/or translational control to suppress, enhance, or otherwise modify the transcription and/or expression of an endogenous gene within the plant. It will be appreciated that control of gene expression can have a direct impact on the observable plant characteristics. Other functional "genes" include sense and anti-sense DNA sequences which may be prepared to suppress or otherwise modify the expression of endogenous genes. The use of anti-sense is described generally in van der Krol et al., (1990) Mol. Gen. Genet. 220:204-212, the disclosure of which is incorporated herein by reference. The use of sense DNA sequence(s) is described in various references, including Napoli et al. (1990) Plant Cell, 2:279-289 and van der Krol et al.

(1990) Plant Cell, 2:291–299, the disclosures of which are incorporated herein by reference.

Structural and regulatory genes to be inserted may be obtained from depositories, such as the American Type Culture Collection, Rockville, Md. 20852, as well as by isolation from other organisms, typically by the screening of genomic or cDNA libraries using conventional hybridization techniques, such as those described in Maniatis et al., *Molecular Cloning—A Laboratory Manual,* Cold Spring Harbor Laboratory, Cold Spring Harbor, N.Y. (1985). Screening may be performed by (1) nucleic acid hybridization using homologous genes from other organisms, (2) probes synthetically produced to hybridize to particular sequences coding for desired protein sequences, or (3) DNA sequencing and comparison to known sequences. Sequences for specific genes may be found in various computer databases, including GenBank, National Institutes of Health, as well as the database maintained by the U.S. Patent Office.

The genes of interest may also be identified by antibody screening of expression libraries with antibodies made against homologous proteins to identify genes encoding for homologous functions. Transposon tagging can also be used to aid the isolation of a desired gene. Transposon tagging typically involves mutation of the target gene. A mutant gene is isolated in which a transposon has inserted into the target gene and altered the resulting phenotype. Using a probe for the transposon, the mutated gene can be isolated. Then, using the DNA adjacent to the transposon in the isolated, mutated gene as a probe, the normal wild-type allele of the target gene can be isolated. Such techniques are taught, for example, in McLaughlin and Walbot (1987) Genetics, 117:771–776; Dooner et al. (1985) Mol. Gen. Genetics, 200:240–246; and Federoff et al. (1984) Proc. Natl. Acad. Sci. USA, 81:3825–3829, the disclosures of which are incorporated herein by reference.

Particular genes which may be incorporated into pea plants according to the method of the present invention include the insect resistance gene (Vaeck et al. (1987) Nature 328:33) and bacterial chitinase genes (Jones et al. (1986) EMBO J. 5:467–473).

The selectable plant marker gene on the DNA sequences to be inserted will usually encode a function which permits the survival and emergence of transformed shoots in a selective regeneration medium. Usually, the selectable marker gene will encode antibiotic resistance, with suitable genes including the aminoglycoside-3" adenyltransferase (aadA) gene encoding spectinomycin resistance, the streptomycin phosphotransferase (SPT) gene encoding streptomycin resistance, the acetolactate synthetase (ALS) gene encoding chlorsulfuron resistance, the neomycin phosphotransferase (NPT) gene encoding kanamycin resistance, and the hygromycin phosphotransferase (HPT) gene encoding hygromycin resistance. Suitable media for selecting pea shoot material expressing these genes are described hereinbelow.

In addition to the "functional" gene and the selectable marker gene, the DNA sequences may also contain a reporter gene which facilitates screening of the transformed shoots and plant material for the presence and expression of the exogenous DNA sequences. Exemplary reporter genes include β-glucuronidase and luciferase. The use of β-glucuronidase is described in more detail hereinafter.

The exogenous DNA sequences will be introduced to the pea explant material by incubation with Agrobacterium cells which carry the sequences to be transferred within a transfer DNA (T-DNA) region found on a suitable plasmid, typically the Ti plasmid. Ti plasmids contain two regions essential for the transformation of plant cells. One of these, the T-DNA region, is transferred to the plant nuclei and induces tumor formation. The other, referred to as the virulence (vir) region, is essential for the transfer of the T-DNA but is not itself transferred. By inserting the DNA sequence to be transferred into the T-DNA region, introduction of the DNA sequences to the plant genome can be effected. Usually, the Ti plasmid will be modified to delete or inactivate the tumor-causing genes so that they are suitable for use as vector for the transfer of the gene constructs of the present invention. Other plasmids may be utilized in conjunction with Agrobacterium for transferring the DNA sequences of the present invention to callus cells.

The construction of recombinant Ti plasmids may be accomplished using conventional recombinant DNA techniques, such as those described in Maniatis et al., supra. Frequently, the plasmids will include additional selective marker genes which permit manipulation and construction of the plasmid in suitable hosts, typically bacterial hosts other than Agrobacterium, such as *E. coli*. Suitable selective marker genes include tetracycline resistance, kanamycin resistance, ampicillin resistance, and the like.

The genes within the DNA sequences will typically be linked to appropriate transcriptional and translational control sequences which are suitable for the pea plant host. For example, the gene will typically be situated at a distance from a promoter corresponding to the distance at which the promoter is normally effective in order to ensure transcriptional activity. Usually, a polyadenylation site and transcription termination sites will be provided at the 3'-end of the gene coding sequence. Frequently, the necessary control functions can be obtained together with the structural gene when it is isolated from a target plant of other host. Such intact genes will usually include coding sequences, intron(s), a promoter, enhancers, and all other regulatory elements either upstream (5') or downstream (3') of the coding sequences.

Optionally, a binary vector system may be used to introduce the DNA sequences according to the present invention. A first plasmid vector strain would carry the T-DNA sequence while a second plasmid vector would carry a virulence (vir) region. By incubating Agrobacterium cells carrying both plasmids with the pea plant material, infection of the pea explant material can be achieved. See, Hoekema et al. (1983) Nature 303:179–180, the disclosure of which is incorporated herein by reference.

Any one of a number of T-DNA plasmids can be used with such a binary vector system, the only requirement being that one be able to select independently for the two plasmids. The T-DNA plasmid in a preferred embodiment comprises a heterologous promoter which promotes the transcription of a gene(s) within the exogenous DNA fragment(s). Examples include the Cauliflower Mosaic Virus 35S promoter (Odell et al. (1985) Nature, 313:810–812); or 1' promoter and 2' promoter (Velten et al. (1984) EMBO J. 12:2723–2730) or nopaline synthatase (nos) promoter (Depicker et al. (1982) J. Mol. Appl. Genet. 1:561–573).

Suitable Agrobacterium strains include *Agrobacterium tumefaciens* and *Agrobacterium rhizogenes*. While the wild-type *Agrobacterium rhizogenes* may be used, the *Agrobacterium tumefaciens* should be "disarmed," i.e., have its tumor-inducing activity removed, prior to use. Preferred *Agrobacterium tumefaciens* strains include LBA4404, as described by Hoekema et al. (1983) Nature, 303:179-180, and EHA101 as described by Hood et al. (1986) J. Bacteriol., 168:1291-1301. A preferred *Agrobacterium rhizogenes* strain is 15834, as described by Birot et al. (1987) Plant Physiol. Biochem., 25:323-325.

After the Agrobacterium strain(s) carrying the desired exogenous DNA sequence(s) have been prepared, they will usually be cultured for a period of time prior to incubation with the pea explant material. Initially, the Agrobacterium may be cultured on a solid media including nutrients, an energy source, and a gelling agent. Suitable nutrients include salts, tryptone, and yeast extracts, while most sugars are suitable as the energy source, and the gelling agent can be TC agar (0.6-1.54), bactoagar (1-2%), Gel-rite ® (0.15-0.5%), or the like. Suitable media include Minimal A, M9, and L-Broth (LB). A preferred -medium is minimal A as described in detail in the Experimental section hereinafter. Usually, the medium will include an antibiotic to select for Agrobacterium carrying the plasmid DNA sequences, e.g., tetracycline at 1-5 mg/l if the marker is tetracycline resistant.

The Agrobacterium cells are typically cultured for about two to five days, preferably in the dark at about 20° C. to 30° C., and are collected while still a white-creamish color, i.e., before browning, typically by being scraped off the solid medium. The cells are scraped off the medium and suspended in a liquid medium, e.g., Minimal A Medium. The pH should be 6.9-7.1, preferably about 7.0. The bacteria are cultured in liquid medium for 8-36 hours (preferably 12-20 hours) on a shaker (50-200 rpm, preferably 100-120 rpm) at 20-30° C. (preferably 22-28° C., most preferably 28° C.). At the end of this period the bacteria are diluted to an Optical Density (OD) of 0.3 (see Maniatis) and cultured-for 2-6 hours (preferably 4 hours), on a shaker (50-200 rpm, preferably 100-120 rpm) at 20-30° C. (preferably 22-28° C., most preferably 28° C.).

The pea explant material and the Agrobacterium cells carrying the desired exogenous DNA sequence(s) are cocultivated in a suitable cocultivation medium to allow transfer of the DNA sequence(s) to plant cells within the explant material. Shoots are then regenerated directly from the transformed plant cells (i.e., the transformed cells do not pass through an intermediate callus stage) in a suitable selection and regeneration medium. The regenerated, transformed shoots may then be rooted in a suitable rooting medium prior to planting of the resulting whole plantlet in soil. Each of these steps and the media suitable for performing such steps will be described in more detail hereinafter.

The cocultivation medium, the selection and regeneration medium, and the rooting medium, are derived from a general pea medium which comprises nutrients, an energy source, and growth regulators. The nutrients should be in the form of conventional macronutrient and micronutrient salts, including nitrogen and iron. Suitable nutrient salts include MS salts (Murashige and Skoog (1962) Physiol. Plant 15:473-497), B5 (Gamborg et al. (1968) Exp. Cell Res. 50:151-158), White's (White (1934) Plant Physiol. 9:585-600), Kao's (Kao (1977) Mol. Gen. Genet. 150:225-230), KM (Kao and Michayluk (1975) Planta 126:105-110), and the like. Suitable energy sources include sugars, such as glucose, maltose, sucrose, lactose, fructose, sucrose in combination with any of the other named sugars, or mannose. A preferred sugar is sucrose at a level of about 5 to 50 g/l, with molar equivalents of other sugars also being suitable. In some cases, a non-sugar energy source, such as acetate, may also be employed.

The general pea medium may include an auxin and/or cytokinin component. Any auxin, natural or synthetic, may be used, e.g., indole acetic acid (IAA), naphthalene acetic acid (NAA), 2,4-dichlorophenoxy acetic acid (2,4-D) and picloram. Mixtures of auxins may be employed e.g., IAA and NAA. The cytokinin may be selected from any of the known cytokinins, natural or synthetic, and may include, but is not limited to 6-benzyladenine (6-BA), zeatin (ZEA), kinetin (KIN), isopentyladenine (IPA), and thidiazuron (TDZ). Mixtures of auxins and cytokinins may be employed e.g., IAA and 6-BA or NAA and KIN. Generally the auxin will be present in an amount of about 0.05-5 mg/l, and cytokinin in an amount of about 0.1-25 mg/l. When IAA is present, the concentration is about 0.05-1 mg/l (preferably either 0.2 mg/l or 1 mg/l depending on the medium). When NAA is present, the concentration is about 0.02-1 mg/l (preferably 0.2 mg/l). When the cytokinin is 6-BA or KIN, the range of concentration is between 1 and 35 mg/l (preferably 10-30 mg/l, more preferably 10-25 mg/l, most preferably about 15 mg/l); when ZEA is used the concentration range may be 2-50 mg/l (preferably 15-35 mg/l, most preferably about 20 mg/l). TDZ may be used as a cytokinin at concentrations ranging from 0.1-15 mg/l (preferably 0.5-3 mg/l).

Amino acids, such as glycine, may be employed in the general pea medium as a nitrogen source. Other nitrogen sources include ammonium nitrate, potassium nitrate, and sodium nitrate. Various vitamin formulations can be included, e.g., MS vitamins, B5 vitamins, Km vitamins, or combinations of thiamine (0.1-10 mg/l), nicotinic acid (0.5-5.0 mg/l), inositol (10-1000 mg/l), pyridoxine (0.5-5.0 mg/l), folic acid (0.1-3.0 mg/l), and biotin (0.01-0.5 mg/l). Other undefined, complex nutrients may be added e.g., coconut milk, casein hydrolysate, and yeast extract. For solid media, an appropriate amount of solidifying agent may be added to the mixture, e.g. agar or Gel-rite ®. 2-(N-Morpholino) ethanesulphonic acid (1-5mm) may be added as a buffer. In general, media pH should be in the range of about 5.6-5.8, preferably about 5.7.

Prior to cocultivation with the Agrobacterium cells, the explant material prepared as described above should be sterilized to remove contaminating microorganisms. Conveniently, sterilization can be achieved by washing with a sterilization medium including a suitable bacteriostat, such as sodium hypochlorite, mercuric chloride, an alcohol, or the like. A preferred sterilization medium includes sodium-hyochlorite at a concentration in the range from about 1 to 2%, preferably about 1.5%, and a detergent, such as Tween ® 80, at from about 0.1-0.3% to reduce surface tension. The pea explant material is then sterilized by immersion in the sterilization medium for a suitable time period, e.g., for about 20 to 45 minutes, either with or without agitation. The pea explant material is then removed from the sterilization medium and washed in distilled water, usually at least twice. All subsequent manipulations of the explant material should be carried out in a sterile environment, e.g., under a laminar air flow hood.

The sterilized pea explant material is then combined with the Agrobacterium cells suspended in a cocultivation medium as follows. Cocultivation medium is the same as the general pea medium except that a virulence (vir) region induction compound is preferably included to induce the vir region of the Agrobacterium cells to enhance transformation efficiencies. Suitable vir induction compounds include acetosyringone (3′,5′-dimethoxy-4′-hydroxyacetophenone, AS) at concentrations between 10–300 μM (200 μM preferred). Instead of AS, any phenolic compound known to the art can be used at comparable molar concentrations; See Bolten et el. (1986) Science 232:983–985.

In addition to the virulence induction compound, a preferred cocultivation medium according to the present invention will utilize sucrose as the energy source (preferably at about 30 g/l), 6-BA as the cytokinin (usually at 1–35 mg/l, preferably at 10–30 mg/l, and more preferably at 10–25 mg/l, and most preferably at about 15 mg/l). IAA may be used as the auxin at about 1 mg/l. The use of B5 salts is also preferred, and abscisic acid can also be added at 0.25 mg/l. A particularly preferred cocultivation medium is C10BA.AS, as set forth in the Experimental section hereinafter.

Prior to introduction to the cocultivation medium, the pea explants are combined with the Agrobacterium cells in a suspension in the bacterial culture medium, where the cells are typically present at from about $10^7$ to $10^9$ cells/ml, preferably at about $5 \times 10^8$ cells/ml. Conveniently, about 200 explants may be combined with about 5 mls of the Agrobacterium cell suspension. The explants are allowed to remain in the suspension for a time sufficient for the explants to become coated with the Agrobacterium cells, usually from about 5 seconds to 10 minutes, preferably being about 5 minutes.

After becoming coated with the Agrobacterium cells, the explant material is transferred to the cocultivation medium where the explants and Agrobacterium cells are cocultured (preferably in the dark) at 20–30° C. (preferably about 24° C.) for a period from about 2–5 days (preferably about 3 days).

After the cocultivation, the Agrobacterium cells are separated from the explant material, preferably by washing with the liquid medium containing an antibiotic which is lethal to the Agrobacterium and non-toxic to the explant material. Suitable antibiotics include carbenicillin (200–1000 mg/l, preferably about 500 mg/l). cefotaxime (200–1000 mg/l, preferably about 500 mg/l), vancomycin (100–500 mg/l, preferably about 100 mg/l). erythromycin (200–1000 mg/l), and amoxicillin (50–500 mg/l). Combinations of these antibiotics may also be used. A preferred combination is about 500 mg/l cefotaxime, about 500 mg/l carbenicillin and about 100 mg/l vancomycin. Explants are mixed well with the liquid medium in a petri dish and agitated on a shaker at about 30–100 rpm (preferably about 60 rpm) at a ratio of about 100 explants to about 25 ml of liquid medium. The liquid medium is replaced with about 25 ml of the same liquid medium after 1 hour, 1–5 times (preferably 3).

The washed explant material is then transferred to a selection and regeneration medium for shoot induction. The selection and regeneration medium has generally the same composition as the cocultivation medium, described above, but does not contain AS, and will usually further include an anti-Agrobacterium antibiotic in order to kill any remaining Agrobacterium cells. The preferred anti-Agrobacterium antibiotic is carbenicillin, usually at about 500 mg/l.

The selection and regeneration medium will usually further comprise an agent to select for transformed shoots. As described hereinabove, the exogenous DNA sequence(s) will usually include a selectable marker, such as the aadA gene, the SPT gene, the ALS gene, the NPT gene, and HPT gene, or the like. Suitable selection agents for these genes will be spectinomycin (100–2000 mg/l, preferably 250–1500 mg/l, more preferably 500–1200 mg/l, most preferably about 500 mg/l), streptomycin (250–5000 mg/l, preferably 250–3000 mg/l, more preferably 500–2500 mg/l, most preferably about 500 mg/l), chlorsulfuron (1–1000 μg/l, preferably 5–100 μg/l, more preferably 15–60 μg/l, most preferably about 50 μg/l), kanamycin (10–1000 mg/l, preferably 25–500 mg/l, more preferably 50–250 mg/l, most preferably about 250 mg/l) and hygromycin (1–500 mg/l, preferably 5–250 mg/l, more preferably 10–100 mg/l, most preferably about 50 mg/l), respectively. Sucrose is the preferred sugar at 30 g/l. A particularly preferred selection and regeneration medium specific for expression of the aadA gene is C10BA500Sp, as described in the Experimental section hereinafter.

The washed explant material is transferred to the regeneration medium typically at about 15 explant pieces in 25 ml of regeneration medium in a 10 cm petri dish. The explants are cultured for 20–90 days (preferably 30–45 days) at 20–25° C. (preferably 24° C.), either in a light regime where during each day of the culture period the mixture is cultured for 16 hrs at 1500–3000 lux under plant spectrum lights and for 8 hrs in a dark growth room, or in the dark for 10–14 days and then transferred to the light regime detailed above. Callus may form on the explants on regeneration medium in approximately 7 days, but the callus will generally not form shoots. Shoot regeneration occurs after about 5–6 weeks. Shoots suitable for rooting according to the present invention will have regenerated directly from the explant with no visible callus phase, and are distinct from any callus which may form. The shoots may form as single shoots or as clumps of shoots from a single transformation event. Transformed shoots produced on spectinomycin, streptomycin or chlorsulfuron containing medium are fully green. Spectinomycin and streptomycin may either inhibit production of nontransformed shoots or may allow production of bleached nontransformed shoots. Chlorsulfuron may be used to inhibit production of nontransformed shoots.

Green shoots that are produced on the explant material in the regeneration medium are excised and transferred to a suitable rooting medium, as follows. The rooting medium is the same as the general pea medium, with the use of MS salts and B5 vitamins being preferred. Sucrose is the preferred sugar (preferably at 30 g/l), with a mixture of the auxins NAA (0.1–0.5 mg/l, preferably about 0.2 mg/l) and IAA (0.1–0.5 mg/l, preferably about 0.2 mg/l) being preferred. Preferably, no cytokinin is included in the rooting medium. Optionally the rooting medium may comprise the plant selection agent described above for the selection and regeneration medium.

The excised shoots are transferred directly to the rooting medium. If a clump of shoots is produced on the regeneration medium, the clump is excised from the regeneration medium and transferred to rooting medium. The shoots and the clumps of shoots are cultured on regeneration medium for 10–40 days (preferably about 30 days) at 20–25° C. (preferably about 24° C.) in a light regime where, during each day of the culture period, the mixture is cultured for 16 hrs at 1500-3000 lux under plant spectrum lights and for 8 hrs in a dark growth room. After incubation, the shoots are transferred to fresh rooting medium under the same conditions as described above. This transfer to rooting medium may be repeated 2-5 times, until roots are formed on the shoots, or from the shoots that grew out of the shoot clumps.

The rooted shoots can then be transplanted to soil within a greenhouse or elsewhere in a conventional manner for tissue culture plantlets. Transformation of the resulting plantlets can be confirmed by assaying the plant material for any of the phenotypes which have been introduced by the exogenous DNA. Suitable assay techniques include polymerase chain reaction (PCR), restriction enzyme digestion, Southern blot hybridization, and Northern blot hybridization.

Particular methods for confirming shoot transformation derived from explant material treated by the method of the present invention are as follows. Transformation may be confirmed by putting the shoot in rooting medium comprising a selection agent. Transformed shoots containing the genes aadA or SPT on rooting medium containing spectinomycin or streptomycin, respectively, produce roots, and new leaf growth is green; nontransformed shoots may have reduced or no root growth and new growth of leaves is white. Transformed shoots containing the gene ALS, NPT or HPT in rooting medium containing chlorsulfuron, kanamycin or hygromycin respectively produce roots, and shoot growth is normal; nontransformed shoots on chlorsulfuron, kanamycin or hygromycin produce no roots and may die.

Confirmation may also be accomplished by removing leaf pieces from the transformed shoots and placing them on a callus induction medium. Callus induction medium is the same as general pea medium, further including a selection agent. MS salts are preferred. B5 vitamins are preferred. Sucrose is preferred as sugar (preferably at about 30 g/l). 6-BA is preferred as cytokinin, at 0.1-5 mg/l (preferably about 0.5 mg/l). NAA at 0.1-3.0 mg/l (preferably about 1.0 mg/l) and 24-D at 0.01-0.5 mg/l (preferably about 0.1 mg/l) are preferred as auxins. A mixture of NAA and 2,4-D at preferred concentrations is preferred. If the callus induction medium contains kanamycin, hygromycin or chlorsulfuron, leaf pieces from transformed shoots containing NPTII, HPT or ALS respectively will form callus on callus induction medium in about 14-21 days; leaf pieces from nontransformed shoots will not form callus. A preferred callus induction medium is CCM, as described in detail in the Experimental section hereinafter.

The following examples are offered by way of illustration and not by way of limitation.

| EXPERIMENTAL MATERIALS | |
|---|---|
| Abbreviations/Names | Source/Reference |
| aadA; Aminoglycoside-3″ Adenyltransferase Gene | Svab et al. (1985) Pl. Mol. Biol. 14:197-205 |
| ALS; Acetolactate Synthetase Gene | Haughn et al. (1988) Mol. Gen. Genet. 211:266-271 |
| Agarose | Type 1; Sigma Chemical Co., St. Louis, MO, USA |
| AS; Acetosyringone | Aldrich Chemical Co., Milwaukee, WI, USA |
| B-5 Salts and vitamins | Gamborg et al. (1968) Exp. Cell Res. 50:151-158 |
| BA (6-BA); Benzyl | Sigma Chemical Co., |
| Adenine | St. Louis, MO, USA |
| Bactogar | Difco Laboratories, Detroit, MI, USA |
| Carbenicillin | Duchefa, Haarlem, Holland |
| Chlorsulfuron; Glean. | E. I. DuPont de Nemours & Co., Wilmington, DE, USA |
| Cefotaxime | Calbiochem Corp., La Jolla, CA, USA |
| 2,4-D; 2,4-Dichloro-phenoxyacetic Acid | Sigma Chemical Co., St. Louis, MO, USA |
| Gel-rite ® | Scott Lab. Inc., Warwick, RI, USA |
| GUS; β-glucuronidase | Jefferson et al. (1986) Proc. Natl. Acad. Sci. USA 83:8447-8451 |
| HPT; Hygromycin Phosphotransferase Gene | van den Elsen et al. (1985) Pl. Mol. Biol. 5:299-302 |
| Hygromycin | Calbiochem Corporation, LaJolla, CA, USA |
| IAA; Indole-3-Acetic Acid | Sigma Chemical Co., St. Louis, MO, USA |
| MES, 2-N Morpholino-ethanesulfonic Acid | Sigma Chemical Co., St. Louis, MO, USA |
| MS Salts | JRH Bioscience, Lenexa, KS, USA |
| NAA, Naphthalene Acetic Acid | Sigma Chemical Co., St. Louis, MO, USA |
| Parafilm | American National Can Co., Parafilm Products, Greenwich, CT, USA |
| PCR; Polymerase Chain Reaction | Saiki et al. (1985) Science 230:1350-1354 |
| Sodium Hypochlorite Bleach | All Pure Chemical Co., Tracy, CA, USA |
| Spectinomycin dihydrochloride | Sigma Chemical Co., St. Louis, MO, USA |
| SPT; Streptomycin Phosphotransferase Gene | Jones et al. (1987) Mol Gen. Genet. 210:86-91 |
| Streptomycin Sulfate | Sigma Chemical Co., St. Louis, MO, USA |
| Tetracycline | Sigma Chemical Co., St. Louis, MO, USA |
| Triton, TritonX-100 | Sigma Chemical Co., St. Louis, MO, USA |
| Tween ® | ICI United States, Inc., Wilmington, DE, USA |
| Vancomycin | Sigma Chemical Co., St. Louis, MO, USA |

| MEDIA COMPOSITIONS | |
|---|---|
| PGM | |
| MS salts | 0.1x |
| B5 vitamins | 1x |
| sucrose | 5 g/l |
| MES | 0.586 g/l |
| agarose | 7 g/l |
| pH | 5.7 |
| Minimal A | |
| $K_2HPO_4$ | 10.5 g/l |
| $(NH_4)_2SO_4$ | 1.0 g/l |
| Na citrate | 0.5 g/l |
| $MgSO_4$ | 0.25 g/l |
| glucose | 2.0 g/l |
| Bactoagar | 15 g/l |
| C medium | |
| B5 salts | 1x |
| B5 vitamins | 1x |
| sucrose | 30 g/l |
| MES | 0.586 g/l |
| pH | 5.7 |
| For solid media | add 4 g/l agarose |
| C10BA | |
| C medium plus 10 mg/l 6-BA | |
| C10BA.AS | |
| C10BA plus 200 μM acetosyringone | |
| C10BA500Sp | |
| C10BA plus 500 mg/l spectinomycin and 500 mg/l carbenicillin | |
| PRM | |

-continued

| | |
|---|---|
| MS salts | 1/2x |
| B5 vitamins | 1x |
| sucrose | 10 g/l |
| MES | 0.586 g/l |
| NAA | 0.2 mg/l |
| IAA | 0.2 mg/l |
| Gel-rite ® | 2.5 g/l |
| pH | 5.7 |
| Basal MS medium | |
| MS salts | 1x |
| B5 vitamins | 1x |
| sucrose | 30 g/l |
| MES | 0.586 g/l |
| agarose | 4 g/l |
| pH | 5.7 |

For CCM:
Basal MS medium plus 0.1 mg/l 6-BA, 1.0 mg/l NAA, 0.1 mg/l 2,4-D

For BIA:
Basal MS medium plus 1 mg/l 6-BA, 1 mg/l IAA, 0.26 mg/l 2,4-D

METHODS AND RESULTS

Example 1

1.1. Explant Source

Mature seed of *Pisum sativum* c.v. Sugar Snap (W. Atlee Burpee Co., Warminster, Pa.) were surface sterilized in a solution containing 1.5% sodium hypochlorite and 0.3% Tween ®80 for 30 minutes on a rotary shaker (50 rpm). The seed were then rinsed three times in sterile double distilled water, and left in the water overnight to imbibe.

1.2. Preparation of Agrobacterium Inoculum

Figure 3:
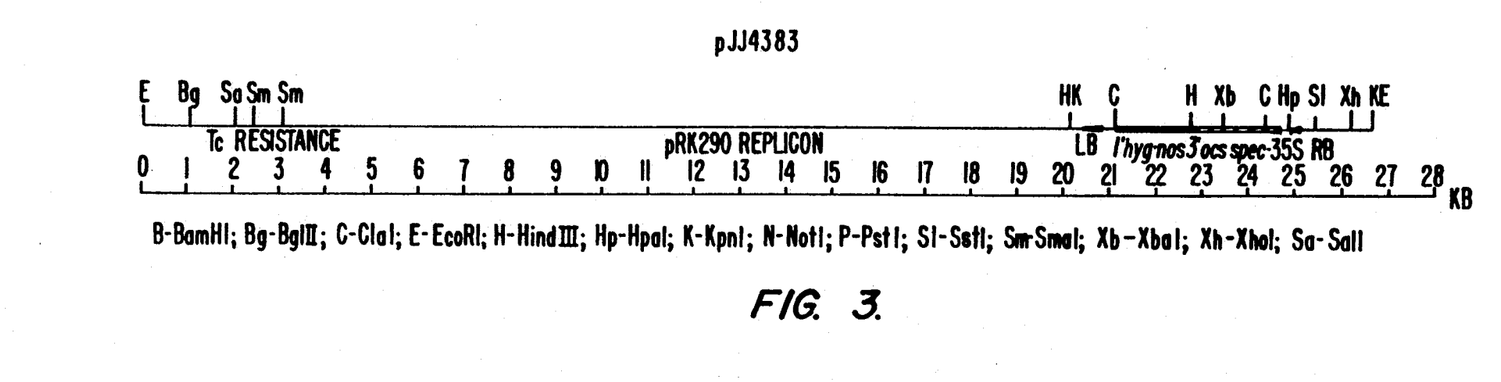

*Agrobacterium tumefaciens* strain LBA4404 (Hoekema, 1983, Nature 303:179-181) containing the binary vector pJJ4383 (FIG. 3) which contains the Cauliflower Mosaic Virus 35S promoter (Odell et al. (1985) Nature 313:810-812) with the aadA gene which confers spectinomycin resistance and the 11 promoter (Velten et al. (1984) EMBO J. 12:2723-2730) with the HPT gene that confers hygromycin resistance. The Agrobacterium cells were maintained on Minimal A plates supplemented with 2.0 mg/l tetracycline. Overnight suspensions were initiated by the addition of a single bacterial colony to three mls of liquid Minimal A in a 30 ml test tube. The tube was cultured on a rotary shaker (150 rpm) overnight at 28° C. in continuous light. An inoculum of approximately $1 \times 10^9$ cells/ml was used.

1.3. Preparation of Explants

Seed coats were removed from approximately 40 of the sterile seed described in Section 1.1, and the cotyledons were separated from the embryonic axes. The embryonic axes were cut into approximately 1 Mm explants and were maintained in liquid c medium prior to inoculation.

1.4. Inoculation and Cocultivation of Explants

The liquid C medium was removed by pipetting and half the explants were transferred to cocultivation medium, specifically C medium containing 10 mg/l 6-BA and 200 mM AS (C10BA.AS). These represented the non-inoculated controls. The bacterial suspension was pipetted onto the remaining explants and the plates were swirled for 5 minutes. The suspension was removed by pipetting and the explants were transferred to the C10BA.AS cocultivation medium. Both the control and the inoculated explants were cultured at 24° C. for three days in a light regime where during each day of the culture period, the explants were cultured for 16 hrs at 1500-3000 lux under plant spectrum lights and for 8 hrs in a dark growth room.

1.5. Selection of Regenerated Shoots

Following the cocultivation period, all explants were washed in liquid C medium supplemented with 500 mg/l carbenicillin, 500 mg/l cefotaxime and 100 mg/l vancomycin. After three one-hour washes, the explants were transferred to selection medium, specifically C medium containing 10 mg/l 6-BA (C10BA) solidified with 0.4% Type I agarose and either 0, 50, 100, 500, or 1000 mg/l spectinomycin dihydrochloride, and 500 mg/l carbenicillin, with approximately 30 explants on each level of spectinomycin. Plates were wrapped with Parafilm and cultured in the same conditions as described in section 1.4. After about three weeks bleached callus and bleached shoots appeared on the non-inoculated explants. The inoculated explants produced both bleached and green callus as well as bleached shoots within the three weeks. After five weeks, a green shoot had formed on selection medium containing 500 mg/l spectinomycin. The shoot formed directly from the surface of the explant completely independent of the calli forming on other regions of the same explant.

1.6. Results

One transformed plant was produced on selection medium containing 500 mg/l spectinomycin. It was analysed by PCR using 20 mer oligos designed to detect a 940 bp fragment of the HPT gene. The expected band was detected. The transformation efficiency (number of confirmed shoots divided by the total number of inoculated explants) was $(1/120) \times 100 = 0.8\%$.

The transformant was further confirmed using a callus assay. The upper portion of the transformant was cut into 2 mm explants and placed on callus induction medium, specifically CCM containing 50 mg/l hygromycin. Non-inoculated, non-selected control explants were also placed on CCM. After two weeks, the explants were assayed for callus growth, and it was found that explants of the transformant had produced significant amounts of green callus while controls were bleached and void of callus. The lower portion of the transformant was placed on a shoot proliferation medium, specifically BIA medium, to produce additional clones of the transformant. These clones were rooted by several passages on a rooting medium, specifically PRM. The plants were then transferred to soil, hardened off, and allowed to flower in the greenhouse. F1 hybrid seed were analysed by PCR for the presence of the HPT gene. The PCR was positive indicating that the introduced genes have been passed to the next generation.

EXAMPLE 2

This Example is as in Example 1 except that the selection medium was C medium containing 500 mg/l spectinomycin and 10 or 25 mg/l 6-BA. One transformed plant was obtained on the selection medium containing 10 mg/l 6-BA, giving a transformation efficiency of 0.25%. Two transformants were obtained on the selection medium containing 25 mg/l 6-BA, giving a transformation efficiency of 0.48%. One of the transformants from 25 mg/l 6-BA was tested using PCR and was found to be positive.

Example 3

This Example was performed as in Example 1 except that the cocultivation medium contained either 0 or 15 mg/l 6-BA and the selection medium was C medium containing 500 mg/l spectinomycin and 15 mg/l 6-BA. Four transformed plants were obtained. Two of the four plants were obtained in cocultivation medium containing 0 mg/l 6-BA, and two on the cocultivation medium containing 15 mg/l 6-BA, one of which was tested using PCR and found to be positive. The transformation efficiency was calculated as in section 1.6. and found to be 1.3%.

Example 4

This Example was performed as in Example 1. The selection media were C medium containing 10 mg/l 6-BA, C medium containing 25 mg/l 6-BA, and BIA medium. All selection media contained 500 mg/l spectinomycin and were solidified with Gel-rite ®. One transformed plant was obtained on BIA. It was tested using PCR and found to be positive. The transformation efficiency for BIA selection was calculated as in section 1.6 and found to be 1.3%.

Example 5

This Example was performed as in Example 1 except that the selection medium was basal MS medium solidified with Gel-rite ® and containing 15 mg/l 6-BA, and 300, 600, 900 or 1200 mg/l spectinomycin. One transformed plant was obtained on the selection medium containing 1200 mg/l spectinomycin, giving a transformation efficiency of 1.25%. Three transformed plants were obtained on the selection medium containing 600 mg/l spectinomycin giving a transformation efficiency of 3.8%. One of the plants selected on 600 mg/l spectinomycin was tested using PCR and found to be positive.

Example 6

6.1. Explant Source

The explant source was as in Section 1.1, except the variety was Sugar Daddy (W. Atlee Burpee Co., Warminster, Pa.).

6.2. Preparation of Agrobacterium Inoculum

Figure 4:
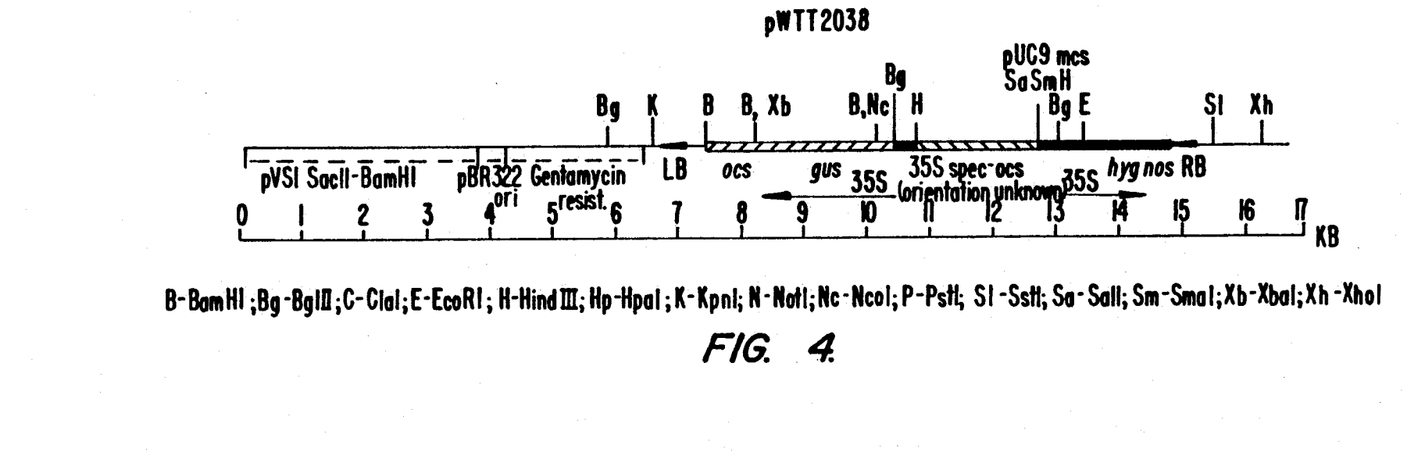
FIG. 4 is a plasmid map of pWTT2038.

Agrobacterium inoculum was prepared as in Section 1.2, except that the binary vector was pWTT2038 (FIG. 4) which contains the 35S promoter driving the aadA gene, the 35S promoter driving the HPT gene, and the 35S promoter driving the GUS gene. The final concentration of the Agrobacterium was $6 \times 10^8$ cells/ml.

6.3 Preparation of Explants

The preparation of the explants was carried out as in Section 1.3, except that instead of the entire embryonic axis, only the lower part of the plumule was used while the radicle and upper part of the plumule were discarded. The lower plumules were cut into halves. The explants were maintained in sterile double distilled water prior to inoculation.

6.4. Inoculation and Cocultivation of Explants

The inoculation and cocultivation of explants was carried out as in Example 1, except that the cocultivation medium was MS medium solidified with Gel-rite ®, supplemented with 15 mg/l BA and 200 μM AS.

6.5. Selection of Regenerated Shoots

The selection was carried out as in Example 1, except that the selection medium was MS medium solidified with Gel-rite ® and supplemented with 15 mg/l BA and 200 mg/l spectinomycin. Culture at 240° C. was in dark conditions for the first 10 days of selection. The plates were then moved to the light conditions as described in section 1.4.

6.6. Results

One transformant was obtained from 150 inoculated explants resulting in a transformation frequency of 0.7%.

Example 7

7.1. Explant Source

Explant source was as in Section 1.1.

7.2. Preparation of Agrobacterium Inoculum

Figure 5:
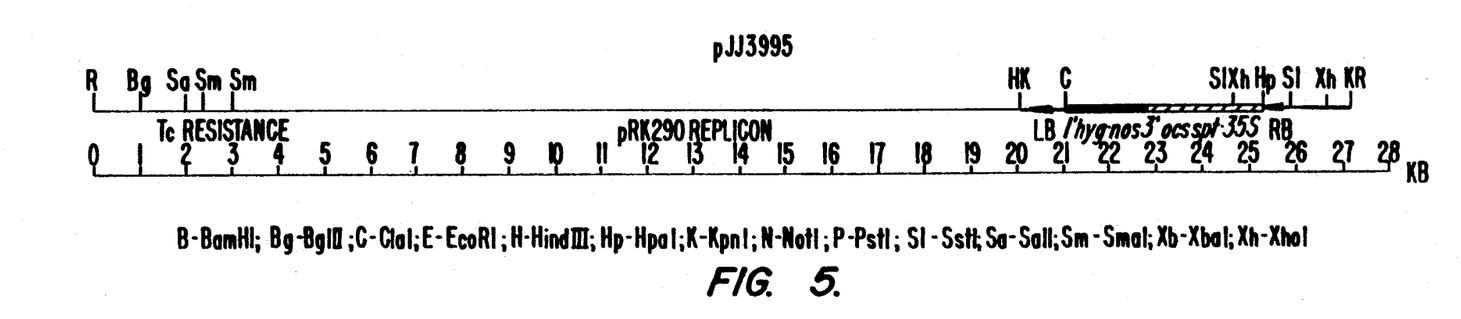
FIG. 5 is a plasmid map of pJJ3995.

Preparation of the Agrobacterium inoculum was as in Section 1.2, except that the binary vector was pJJ3995 (FIG. 5) which contains the 1' promoter driving the HPT gene and the 35S promoter driving the SPT gene that confers resistance to streptomycin.

7.3. Preparation of Explants

Preparation of the explants was carried out as in Section 6.3, except that the lower plumules were cut into three explants per plumule.

7.4. Inoculation and Cocultivation of Explants

The inoculation and cocultivation of explants was carried out as in Section 1.4, except that the cocultivation medium was BIA solidified with Gel-rite ®.

7.5. Selection of Regenerated Shoots

Selection was carried out as in Section 1.5, except that the selection medium was BIA supplemented with 500, 1000 or 1500 mg/l streptomycin sulfate.

7.6. Results

Two transformants were obtained on the selection medium containing 500 mg/l streptomycin. The transformation efficiency was calculated as in Section 1.6 and found to be 0.9%. One of the transformants died prior to maturation. The other was tested using PCR and found to be positive. F1 seed have been obtained.

Example 8

8.1. Explant Source

Explant source was the same as in Section 1.1.

8.2. Preparation of Agrobacterium Inoculum

Figure 6:
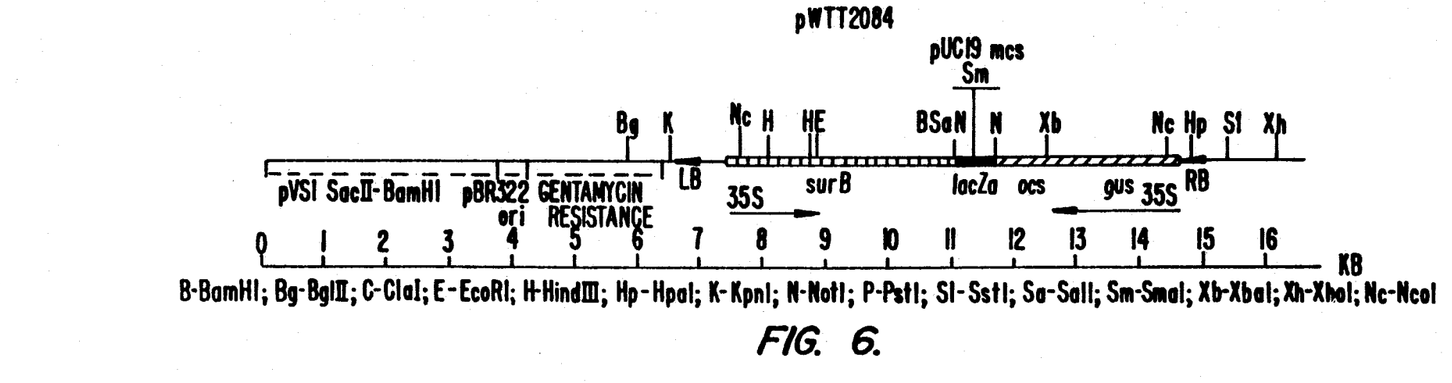
FIG. 6 is a plasmid map of pWTT2084.

The Agrobacterium was prepared as in section 1.2, except that the Agrobacterium tumefaciens strain was EHA101, and it contained the binary vector pWTT2084 (FIG. 6). pWTT2084 contains the 35S promoter driving the ALS gene that confers resistance to chlorsulfuron, and the 35S promoter driving the GUS gene.

8.3. Preparation of Explants

The preparation of explants was carried out as in section 7.3.

8.4. Inoculation and Cocultivation of Explants

The inoculation and cocultivation of the explants was carried out as in Section 1.4, except that the cocultivation medium was solidified with Gel-rite ® and contained 50 μM AS. Cocultivation was for four days.

8.5. Selection of Regenerated Shoots

Selection of regenerated shoots was carried out as in Section 1.5, except that the selection medium was C medium solidified with Gel-rite ® and containing 0, 50 or 200 μg/l chlorsulfuron.

8.6. Results

Three transformants were produced on selection medium containing 50 μg/l chlorsulfuron. The transformation efficiency was calculated as in Section 1.6 and found to be 2.4%. Transformants growing on chlorsulfuron were tested for the presence of the GUS gene by the GUS assay (Jefferson et al. (1986) Proc. Natl. Acad. Sci. USA 83:8447-8451), and were found to be positive.

Example 9

This example is the same as in Example 8 except that the variety was Sugar Daddy and the selection medium was C medium solidified with Gel-rite ® and containing 50 and 75 μg/l chlorsulfuron. Four transformants were obtained, three on 50 μg/l chlorsulfuron and one on 75 μg/l chlorsulfuron, giving transformation efficiencies of 7.7% and 1.8% respectively. Two of the transformants growing on 50 μg/l chlorsulfuron were tested for the presence of the GUS gene and were found to be positive.

Example 10

This example is the same as in Example 8 except that the variety was Oregon Sugar Pod II (W. Atlee Burpee Co., Warminster, Pa.) and the selection medium was C medium solidified with Gel-rite ® and containing 0, 50, 75, 100 or 150 μg/l chlorsulfuron. Three transformants were obtained, one each on 50, 100 and 150 μg/l chlorsulfuron giving transformation efficiencies of 4.2%, 3.8%, and 3.6% respectively. The transformants growing on 50 and 100 μg/l chlorsulfuron were tested for the presence of the GUS gene and were found to be positive.

Although the foregoing invention has been described in detail for purposes of clarity of understanding, it will be obvious that certain modifications may be practiced within the scope of the appended claims.

What is claimed is:

1. A method for genetically transforming a pea plant, said method comprising:
   (a) culturing explant material from the seed plumule of the pea plant with *Agrobacterium tumefaciens* or rhizogenes cells carrying an exogenous DNA sequence, wherein the strain of Agrobacterium is selected to be capable of infecting and transferring DNA to the explant material;
   (b) regenerating shoots from the explant material from step (a), wherein said shoots are obtained from non-callus material;
   (c) selecting regenerated shoots from step (b) which express the exogenous DNA sequence, and
   (d) rooting said regenerated shoots to produce viable pea plants expressing the exogenous DNA sequence.

2. A method as in claim 1, wherein the pea plant is a garden pea plant.

3. A method as in claim 2, wherein the pea plant has an edible pod.

4. A method as in claim 1, wherein the exogenous DNA includes a plant selectable marker gene selected from the group consisting of aadA, SPT, and ALS.

5. A method as in claim 1, wherein the shoots are regenerated in a medium containing an amount of 6-BA selected to induce shoot regeneration.

6. A method as in claim 1, wherein the shoots are regenerated from non-callus material.

7. A method for genetically transforming a pea plant, said method comprising:
   (a) obtaining plumule material from a pea plant seed;
   (b) culturing the plumule material with *Agrobacterium tumefaciens* or rhizogenes cells carrying an exogenous DNA sequence in a cocultivation medium for a time and under conditions selected to effect transfer of the exogenous DNA sequence to cells of the plumule material, wherein the strain of Agrobacterium is selected to be capable of infecting and transferring DNA to the explant material;
   (c) separating the Agrobacterium cells form the plumule material;
   (d) regenerating shoots from the plumule material from step (c) in a regeneration medium for a time and under conditions selected to produce shoots from non-callus regions of the plumule;
   (e) selecting regenerated shoots from step (d) which express the exogenous DNA sequence; and
   (f) rooting the selected regenerated shoots from step (e) in a rooting medium to produce plants which express the exogenous DNA sequence.

8. A method as in claim 7, wherein the plumule material is from the lower region of the plumule.

9. A method as in claim 7, wherein the exogenous DNA sequence includes a plant selectable marker gene selected from the group consisting of aadA, SPT, and ALS.

10. A method as in claim 7, wherein the cocultivation medium contains nutrients, an energy source, and a virulence induction compound.

11. A method as in claim 10, wherein the cocultivation medium further contains a cytokinin.

12. A method as in claim 11, wherein the cytokinin is 6-BA.

13. A method as in claim 7, wherein separating comprises washing the plumule material with an anti-Agrobacterium antibiotic.

14. A method as in claim 7, wherein the regeneration medium contains nutrients, an energy source, and an anti-Agrobacterium antibiotic.

15. A method as in claim 14, wherein the exogenous DNA sequence includes a plant selectable marker and the regeneration medium further contains a plant selection agent which inhibits growth of plant material not expressing said marker.

16. A method as in claim 15, wherein the plant selectable marker is selected from the group consisting of aadA, SPT, and ALS and the plant selection agent is selected from the group consisting of spectinomycin, streptomycin, and chlorsulfuron, respectively.

17. A method as in claim 7, wherein the rooting medium contains nutrients, an energy source, an auxin, and a plant selection agent.

18. A method as in claim 7, wherein the rooting medium is substantially free from cytokinins.

19. A method for genetically transforming a pea plant, said method comprising:
- (a) preparing an explant by removing the seed coat from a sterilized seed of the pea plant and cutting off the cotyledons where they are attached to the embryo;
- (b) culturing explant material from sterilized seed of the pea plant with *Agrobacterium tumefaciens* or rhizogenes cells carrying an exogenous DNA sequence, wherein the strain of Agrobacterium is selected to be capable of infecting and transferring DNA to the explant material;
- (c) regenerating shoots from the explant material from step (a), wherein said shoots are obtained from non-callus material;
- (d) selecting regenerating shoots from step (b) which express the exogenous DNA sequence, and
- (e) rooting said regenerated shoots to produce viable pea plants expressing the exogenous DNA sequence.

20. A method as in claim 19, wherein the pea plant is a garden pea plant.

21. A method as in claim 20, wherein the pea plant has an edible pod.

22. A method as in claim 19, wherein the exogenous DNA includes a plant selectable marker gene selected from the group consisting of aadA, SPT, and ALS.

23. A method as in claim 19, wherein the shoots are regenerated in a medium containing an amount of 6-BA selected to induce shoot regeneration.

* * * * *